United States Patent
Mitsuhashi et al.

[11] Patent Number: 6,120,612
[45] Date of Patent: Sep. 19, 2000

[54] METHOD FOR THE CONTINUOUS MANUFACTURE OF ANHYDROUS CRYSTALLINE MALTITOL AND A MANUFACTURING APPARATUS THEREFOR

[75] Inventors: Masakazu Mitsuhashi, Okayama; Zenichi Yoshino, Kashihara; Toshiaki Komaki, Nishinomiya; Yoshiki Kurahashi, Osaka; Shigemitsu Ohsaki, Kashihara; Hiromasa Ueyama, Kashihara; Makoto Kittaka, Kashihara, all of Japan

[73] Assignees: Kabushiki Kaisha Hayashibara Seibutsu Kagaku Kenkyujo, Okayama; Sanwa Kosan Kabushiki Kaisha, Kashihara, both of Japan

[21] Appl. No.: 09/237,783

[22] Filed: Jan. 26, 1999

[30] Foreign Application Priority Data

Jan. 27, 1998 [JP] Japan ................................. 10-030613

[51] Int. Cl.⁷ ................................. C13P 1/02; B01D 9/02

[52] U.S. Cl. ................................. 127/60; 127/16

[58] Field of Search ................................. 127/16, 60

[56] References Cited

FOREIGN PATENT DOCUMENTS

| 5823799 | of 0000 | Japan . |
| 5617078 | of 1972 | Japan . |
| 56-11437 | of 1981 | Japan . |
| 632439 | of 1982 | Japan . |
| 579316 | of 1985 | Japan . |
| 211599 | of 1989 | Japan . |
| 714953 | of 1992 | Japan . |
| 5-2320 | of 1993 | Japan . |
| 6277100 | of 1994 | Japan . |

*Primary Examiner*—David Brunsman
*Attorney, Agent, or Firm*—Roland Plottel

[57] ABSTRACT

Disclosed herein is a continuous manufacturing method for anhydrous crystalline maltitol comprising the following steps: (i) a heating and concentrating step where an aqueous solution containing maltitol in which maltitol is a main ingredient is continuously heated and concentrated to give a concentrated solution having a high concentration; (ii) a seed crystal adding and mixing step where the seed crystals are added to and mixed with the above concentrated solution with heating to give a massceuite containing the seed crystals; and (iii) a crystal aging step where the massceuite is subjected to disintegration, mixing, stirring and transfer in an atmosphere in which temperature and moisture are adjusted to proceed the crystallization.

9 Claims, 1 Drawing Sheet

1 CONCENTRATION APPARATUS
2 SEED CRYSTAL TANK
3 CONTINUOUS FLOW FEEDER
4 SEED CRYSTAL MIXER
5 CRYSTAL AGING MACHINE

1  CONCENTRATION APPARATUS
2  SEED CRYSTAL TANK
3  CONTINUOUS FLOW FEEDER
4  SEED CRYSTAL MIXER
5  CRYSTAL AGING MACHINE

METHOD FOR THE CONTINUOUS MANUFACTURE OF ANHYDROUS CRYSTALLINE MALTITOL AND A MANUFACTURING APPARATUS THEREFOR

TECHNICAL FIELD OF THE INVENTION

The present invention relates to a method and an apparatus for the manufacture of stable anhydrous crystalline maltitol on a total amount method (may be called a total sugar method as well) on a continuous basis. More particularly, the present invention relates to a method for the manufacture of stable anhydrous crystalline maltitol within short time wherein a step of heating and concentrating an aqueous solution containing maltitol, a step of producing a seed crystal-containing supersaturated substance (massceuite) by adding and mixing seed crystals to and with the concentrated maltitol solution, a step of aging the crystals for proceeding the crystallization at high temperature and increased humidity, etc. are continuously conducted and also to an apparatus used therefor. The anhydrous crystalline maltitol used in the present invention may be anything so far as it is a substantially non-hygroscopic or hardly hygroscopic crystalline maltitol and, in addition to such an anhydrous crystalline maltitol, it may also be molasses-containing crystals which contains a sugar alcohol such as sorbitol, maltotriitol and maltotetraitol or a saccharide such as glucose and fructose.

PRIOR ART

Maltitol crystals are inherently highly hygroscopic and there have been considerable investigations on a method for the manufacture of non-hygroscopic crystalline powder. For example, a method for the manufacture of anhydrous crystalline maltitol or anhydrous crystalline maltitol molasses-containing crystals is mentioned in the Japanese Examined Patent Publication Sho-63/2439B. Details of that method are as follows. Thus, a solution of maltitol for crystallization is made in a degree of supersaturation of about 1.05–1.5 and, to be more specific, maltitol having a purity of not less than 65% is made into an aqueous solution of about 65–95% concentration, such a supersaturated maltitol solution of a relatively high temperature of 45–95° C. is charged in a crystallizing vessel, then 0.1–20% of seed crystals are added thereto and the mixture is slowly cooled with gentle stirring for promoting the crystallization whereupon massceuite is obtained. Known method such as molasses separation method, block disintegrating method, fluid granulating method and spray drying method may be utilized as a method for collecting anhydrous crystalline maltitol and molasses-containing crystals which contain the anhydrous crystalline maltitol from the crystallized massceuite.

For example, a molasses separation method is usually a method in which a massceuite is charged in a centrifugal separator of a basket type to separate into anhydrous crystalline maltitol and molasses. If necessary, said crystals may be easily washed by means of spraying a small amount of cold water thereon and such a method is suitable for the manufacture of non-hygroscopic anhydrous crystalline maltitol having a high purity. In the case of a spray drying, a massceuite having a concentration of 70–85% and degree of crystallization of about 25–60% is sprayed from a nozzle using a high-pressure pump, dried with hot air of such a temperature that the crystal powder is not melted (for example, 60–100° C.) and aged using warm air of 30–60° C. for about 1–20 hours whereupon non-hygroscopic molasses-containing crystals can be easily manufactured. In a block disintegrating method, a massceuite containing 5–15% of water and having a degree of crystallization of about 10–60% is usually allowed to stand for 0.5–5 days so that the whole substance is crystallized out and solidified in blocks and the blocks are disintegrated by means of grinding or cutting and then dried whereupon the non-hygroscopic or hardly hygroscopic molasses-containing crystals can be easily manufactured. It is also possible that, in accordance with conventional method, an aqueous solution of maltitol is heated to concentrate to make the water content less than 5%, then seed crystals are kneaded with the resulting supersaturated maltitol solution in a melted state at the temperature of not higher than the melting point of maltitol and the kneaded mixture is made into various shapes to give non-hygroscopic or hardly hygroscopic molasses-containing crystals.

The above-mentioned methods are described in the specification of the above-identified patent and, in its Examples, the following methods are specifically disclosed. Thus, a method in which a maltitol solution is concentrated to a 80% concentration and charged in an crystallizing vessel, 1% of powdery seed crystals of anhydrous crystalline maltitol are added, the mixture is made 50° C. and allowed to cool with a slow stirring until 20° C. during three days and molasses are separated by a centrifugal machine of a basket type to give anhydrous crystalline maltitol (Example 2); a method in which a maltitol solution is concentrated to a 88% concentration and charged in an crystallizing vessel, 2% of powdery crystals of anhydrous crystalline maltitol are added, the mixture is made at 50° C., kept at that temperature for two hours with a slow stirring, taken out into a vat and allowed to stand at 20° C. for four days and the crystallized and separated product is disintegrated by a grinder of a cutting type followed by drying to give molasses-containing crystal powder of anhydrous crystalline maltitol (Example 3); and a method in which a maltitol solution is concentrated to a 80% concentration, charged in a crystallizing vessel, and admixed with 2% of molasses-containing crystal powder which contains anhydrous crystalline maltitol, the mixture is gradually cooled starting from 50° C. with a slow stirring, the resulting massceuite (degree of crystallization being 35%) is sprayed from a nozzle of 1.5 mm diameter on a drying tower with a pressure of 150 kg/cm$^2$ using a high-pressure pump and, at the same time, hot air of 85° C. is sent from the upper part of the drying tower to collect on a wire net conveyer placed at the bottom of the tower, then the crystalline powder collected on a wire net conveyer is gradually moved to outside of the drying tower together with sending hot air of 40° C. from the bottom of the conveyer, the crystalline powder which is taken out during 40 minutes is filled in an aging tower and aged for ten hours to complete both crystallization and drying whereupon anhydrous crystalline maltitol molasses-containing crystalline powder is obtained (Example 4). However, all of those methods need long time for crystallization or for aging of maltitol crystals and, therefore, there is a disadvantage that it is difficult to make the apparatus simple and continuous.

In the Japanese Examined Patent Publication Hei-07/14953B, there is a disclosure on a method for the manufacture of maltitol molasses-containing crystals as well. In said method, an aqueous solution of maltitol is continuously supplied to an extruder having a slender cooling and kneading zone and subjected to a continuous cooling and kneading in the presence of seed crystals to produce a maltitol magma and the magma is continuously extruded from an extruding nozzle to give maltitol molasses-containing crystals. Although this method is successful in terms of making the operations continuous but an extruder having a slender cooling zone is used and, in order to conduct a highly concentrating process, the temperature becomes inevitably high due to the viscosity. Thus, a crystal production is proceeded by cooling said concentrated solution for increasing the degree of supersaturation and the step is in such a manner that the seed crystals are added thereto and kneaded therewith under cooling and the a maltitol magma produced thereby is discharged from an extruding nozzle.

However, when cooling is accompanied, a highly concentrated maltitol starch syrup becomes highly viscous due to a lowering of the temperature as a result of the cooling and, therefore, a big power is needed for conducting a kneading operation which results in a rise in a running cost. In addition, plural zones [i.e., a cooling/kneading zone for introduction of the material; a zone for adding and mixing the seed crystals; a zone for cooling and kneading after addition of the seed crystals (a maltitol magma producing zone); etc.] are necessary and, therefore, big equipment is required and, further, load of power becomes high because of an increase in viscosity due to cooling. Accordingly, it is predicted that making the size of the apparatus big for an industrial production will be difficult. Moreover, in the case of manufacture of a final product in a powdery state, steps of rough disintegration, aging, drying, etc. of the maltitol magma discharged from the extruding nozzle in various shapes are necessary and, in that case, further long time is needed for the manufacture which causes an increase in the manufacturing cost.

Problems to be Solved by the Invention

In an industrial production of sweet saccharides and the like, a reduction in the product cost has a very important meaning. For such a purpose, it is desired that all steps can be made continuously operated and the labor expenses can be reduced greatly and, in addition, there is a demand for a method wherein all of the product can be crystallized without giving by-products and the product is stable in terms of hygroscopicity, etc.

In the crystallization of saccharides, it is desirable that all of the steps are to be made continuously operated. Such steps include a step where a supersaturated solution is obtained by means of concentration, a step where the temperature which is convenient for crystallization is maintained and crystallization is promoted by adding the seed crystals, an aging step for further growth of the crystals and, if necessary, a step where they are pulverized and sieved. For such a purpose, it is necessary to find a condition whereby each of the steps is completed within short time.

The present inventors have previously developed a method for the manufacture of water-containing crystalline β-maltose as disclosed in the Japanese Examined Patent Publication Hei-05/79316B, then developed a method for a continuous crystallization of whole of anhydrous crystalline α-maltose and succeeded in manufacturing it in an industrial scale as disclosed in the Japanese Laid-Open Patent Publication Hei-06/277100A and, after that, they have conducted in developing a continuous manufacturing method for anhydrous crystalline maltitol.

The present inventors have had an idea that the continuous operation will be possible and the production cost can be significantly reduced if the problem that long time is needed in aging of crystals which is a disadvantage factor in the conventional method as disclosed in the Japanese Examined Patent Publication Sho-63/2439B can be solved and they have continued the invention on this respect. To be more specific, various investigations have been conducted with a target of conducting the following steps continuously. They are a step where a solution containing anhydrous maltitol is concentrated, a step where an appropriate amount of seed crystals is added thereto to give a supersaturated product containing the seed crystals (massceuite) and a step where aging is conducted for completing the crystallization in the massceuite.

In a concentrating method where the material solution is made supersaturated in terms of anhydrous maltitol, it is possible to give a desired degree of concentration by the use of a concentrating apparatus of a thin film type and the problem is that how to complete the crystallization within short time. Under such a condition that long time is required for completing the crystallization, the volume of the apparatus becomes large even if making the steps continuous is successful and, therefore, such a method is not practical in terms of apparatus and economy as well. The present inventors have previously succeeded in continuously conducting the crystallization of the whole amount of anhydrous crystalline α-maltose and they have now found that anhydrous crystalline maltitol is crystallized more easily as compared with the above-mentioned one.

Means for Solving the Problems

The present inventors have investigated how the total steps for crystallization of maltitol can be reduced in terms of time and found that, with regard to the crystallization, it is necessary that the seed crystals are homogeneously mixed within short time. With this respect, there are many examples that, usually, an increase in the degree of supersaturation by cooling is adopted as the condition for crystallization while the present inventors have now found that it is advantageous that the viscosity is reduced by heating the solution of a high concentration at high temperature whereby the seed crystals are homogeneously dispersed within short time. The present inventors have further found that, when maltitol concentration in an aqueous solution of maltitol is concentrated to an extent of not lower than a certain concentration and when the environment for the step for aging the crystals after crystallization is controlled, it is now possible that time for crystallization can be greatly shortened and the steps can be easily made continuous.

The present invention is characterized, based upon the above findings, in consisting of a heating and concentration step where a concentrating apparatus is used, a seed crystal adding and mixing step where the seed crystals are added and mixed at high temperature and a crystal aging step where the crystallization is completed and also in adopting specific operation conditions for each of those steps.

Thus, the present invention relates to a continuous manufacturing method for anhydrous crystalline maltitol comprising the following steps:

(i) a heating and concentrating step where an aqueous solution containing maltitol in which maltitol is a main ingredient is continuously heated and concentrated to give a concentrated solution having a high concentration;

(ii) a seed crystal adding and mixing step where the seed crystals are added to and mixed with the above concentrated solution with heating to give a massceuite containing the seed crystals; and (iii) a crystal aging step where the massceuite is subjected to disintegration, mixing, stirring and transfer in an atmosphere in which temperature and moisture are adjusted to proceed the crystallization.

The present invention also relates to a continuous manufacturing apparatus for anhydrous crystalline maltitol comprising the following means:

(i) a heating and concentrating means where an aqueous solution containing maltitol is continuously heated and concentrated to give a concentrated solution having a high concentration;

(ii) a seed crystal adding and mixing means where the seed crystals are added to the concentrated solution by keeping the temperature at not lower than 80° C. to produce a seed crystal-containing massceuite in which the content of the crystals is not less than 40 w/w %; and (iii) a crystal aging means where the massceuite is subjected to disintegration, mixing, stirring and transfer in an atmosphere of temperature of 70–100° C. and absolute humidity of 50–300 g $H_2O$/kg dry air to proceed the crystallization.

BEST MODE FOR CARRYING OUT THE INVENTION

Figure 1:
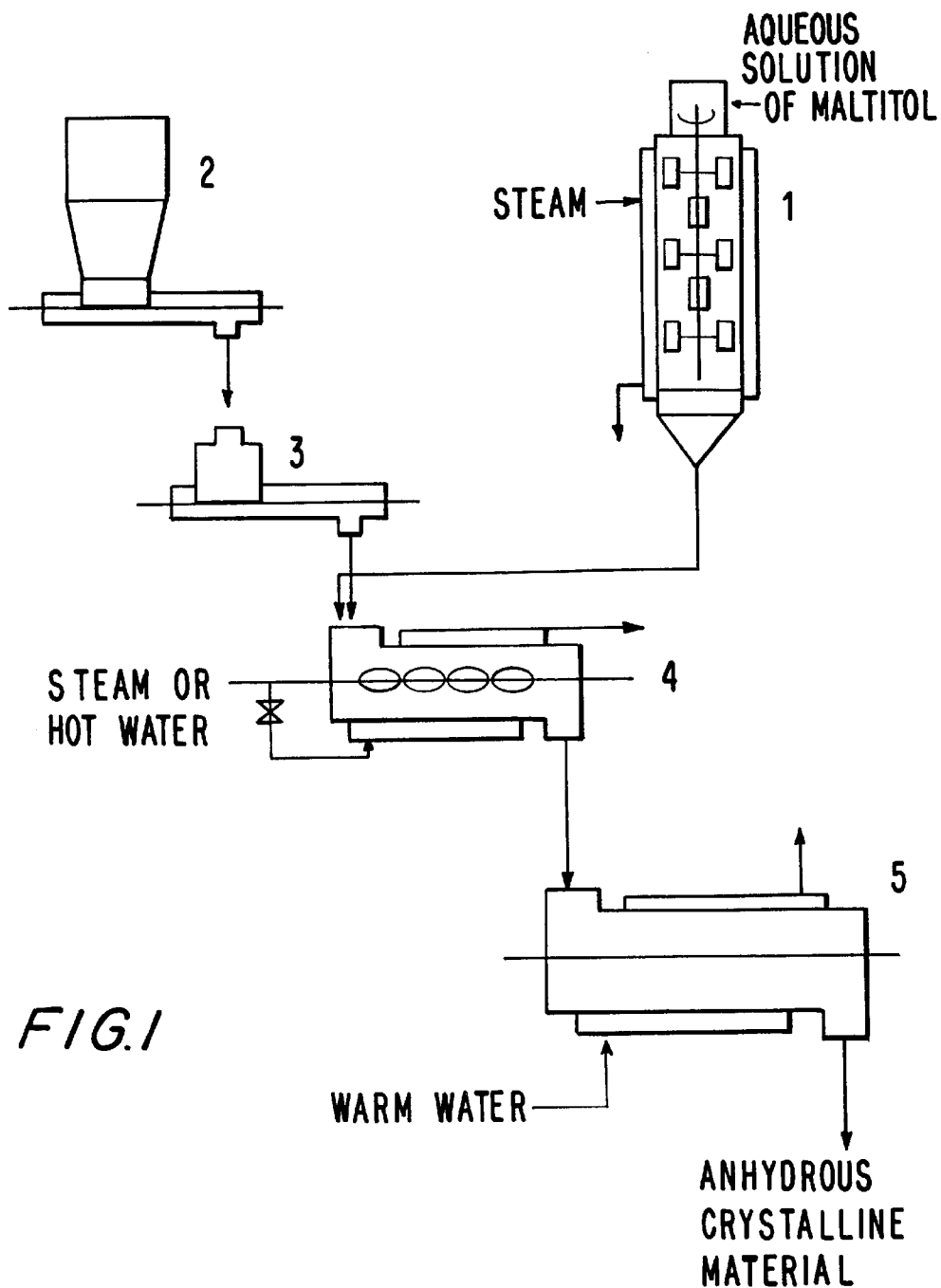
FIG. 1 shows the manufacturing steps of the present invention (Example 1).

There is no particular limitation for preparing an aqueous solution of maltitol used in the present invention and any of the conventionally known methods may be adopted. With regard to the aqueous solution of maltitol, it is preferred that purity of maltitol is not lower than 80 w/w % and the aqueous solutions of maltitol obtained by the following method may be used. Thus, hydrogenation is conducted by adding a Raney nickel catalyst to a highly pure maltose obtained by (1) a method where gelatinized or liquefied starch is treated with β-amylase and the resulting maltose is separated from the high-molecular dextrin to collect a highly pure maltose (Japanese Examined Patent Publications Sho-56/11437B and Sho-56/17078B), (2) a method where gelatinized and liquefied starch is treated with starch debranching enzyme (such as isoamylase and pullulanase) and β-amylase to give a highly pure maltose, or (3) a method where contaminating saccharides such as maltotriose contained in the highly pure maltose prepared by the above methods are removed by a column chromatography method using a strongly acidic cationic ion exchange resin of a salt type disclosed, for example, in the Japanese Laid-Open Patent Publication Sho-58/23799A whereby the purity of maltose is made higher. Alternatively, an aqueous solution of maltitol is subjected to various fractionating methods (Japanese Examined Patent Publication Hei-02/11599B) and the resulting highly pure maltitol may be used for this purpose.

As hereunder, optimum conditions for each of the steps of the present invention will be illustrated in detail.

Firstly, in a concentrating step, it is preferred to use a continuous concentrating machine of a thin film type such as a centrifugal thin-film concentrating apparatus and a vertical thin-film concentrating apparatus although the present invention is not limited thereto. Concentration of maltitol is adjusted using such a concentrating apparatus. The term "concentration of maltitol" used here means the percentage by weight of pure maltitol in the concentrated solution [i.e., (concentration of maltitol)=(concentration of the solid in the concentrated solution)×(purity of maltitol); for example, when purity of maltitol in an aqueous solution of maltitol of 95 w/w % solid concentration is 96 w/w %, then the concentration of maltitol is 95×0.96=91.2 w/w %] and, in the present invention, it is preferred to adjust this concentration to 78–98 w/w %.

Thus, the concentration of maltitol means that, when purity of maltitol in the aqueous solution of maltitol is low, a highly concentrating operation is necessary while, in the case of a maltitol solution of a high purity, a lowly concentrating operation will do. Practically however, when purity of maltitol is as low as not higher than 80 w/w %, it is to be concentrated to an extent of degree of concentration of around 98 w/w % for making the concentration of maltitol 78 w/w % or more and, in that case, the process becomes very slow both in terms of manufacture and crystallizing speed due to its high viscosity and that is contrary to the object of the present invention. Measurement of a concentration of a solid at that time is conducted in such a manner that water content (w/w %) is measured by a Karl-Fischer method and said water content (w/w %) is deducted from 100 to give a concentration of the solid (w/w %). Incidentally, moisture content (based upon a dry substance) is calculated from the water content by a Karl-Fischer method. Purity of maltitol is analyzed by means of a high liquid chromatography by a conventional method.

With regard to the next step of adding and mixing the seed crystals, it is necessary to maintain a high temperature in this step so that the seed crystals are well dispersed in a concentrated solution within short time with heating and further that an increase in viscosity during the mixing and dispersing step is suppressed. In addition, it is preferred that, during this step, there is substantially no evaporation of water. When concentration proceeds as a result of evaporation of water, the viscosity becomes high and a very big driving force is necessary for the apparatus and that is not recommended. Moreover, mixing and dispersing of the seed crystals are deteriorated and, as a result, the crystallizing time in the crystal aging step becomes long. Thus, in view of those, an excessive concentration is not preferred. Usually, the moisture content of the massceuite is preferably at least 3 w/w %.

Further, in this step, a heating apparatus by means of a jacket is necessary for preventing the deterioration of a mixing and dispersing ability as a result of an increase in viscosity due to lowering of the temperature and it is important to keep the low viscosity for dispersing and mixing of the seed crystals within short time. The apparatus which is preferred for such a purpose is a vessel-fixing type or a horizontal axis or horizontal double axis type generally used for kneading a small amount of powder into a highly viscous substance or colloidal substance and is a continuous kneader of a tightly closed type equipped with a heating device in a ribbon system, a screw extrusion system, a self-cleaning system, a paddle system, etc. It is also possible to use by selecting such a one that is suitable for continuous operation from the apparatuses such as kneader or mixer used for mixing or kneading.

Supplement of the seed crystals may be conducted by a method where crystal powder is quantitatively supplied either continuously or intermittently at the inlet of the seed crystal mixer or by a method where a part of the massceuite in which crystallization is proceeded is returned from the outlet of the seed crystal mixer to the inlet of the seed crystal mixer. In that case, it is of course necessary to pay due attention that the temperature does not lower. The seed crystals used are prepared from anhydrous crystalline maltitol and molasses-containing anhydrous crystalline maltitol. The content of the anhydrous crystalline maltitol in this molasses-containing crystals is important since it controls the crystallizing speed and it goes without saying that the higher the content, the higher the crystallizing speed. The amount of the seed crystals to be added may be 0.1 w/w % or more and, although an increase in the amount results in a proportional increase in volume affecting the productivity, that also somewhat relates to the speed of crystal separation and, accordingly, when it is desired to make the whole apparatus compact for a continuous operation for short time which is an object of the present invention, it is preferred to add 5–30 w/w % of the seed crystals to the solid in the concentration solution.

During the course of passing of the seed crystals through the seed crystal mixer, it is the utmost factor that the seed crystals are homogeneously dispersed in the concentrated solution and, during the course of introducing the crystallization to the next crystal aging step, water in the massceuite should not be evaporated substantially. In the common methods (e.g., Japanese Examined Patent Publications Sho-63/2439B and Hei-07/14953B), a crystallizing step consists of separation of crystals by controlling the degree of super-saturation as a result of cooling the temperature for crystallization. However, in the present invention, degree of concentration is made high and the crystallizing temperature is made rather high to make the viscosity low so that the seed crystals are well dispersed by a mechanical stirring whereby this step is completed within very short time. It is particularly characteristic in the step of adding and mixing the seed crystals that the temperature is made high, preferably at 80° C. or higher. Incidentally, when this seed crystal adding and mixing step is completed and is just coming to the next step, the content of the crystals in the massceuite should be at least 40 w/w %.

The next step is an aging step for the crystals which is the most important point in the present invention. In the massceuite mixed with the seed crystals, crystallization starts at several minutes after the mixing to give white solid blocks (massceuite). In the crystal aging step, the blocks are subjected to disintegration, stirring, mixing and transfer (convey) in an atmosphere of a high temperature and a certain humidity whereby they arrives at the outlet of the crystal aging machine together with a progress of the crystallization. Convenient crystal aging machine used here is that which is a continuous kneader type and has an internal space and it is necessary to use an apparatus which is to be able to disintegrate, mix, stir and transfer the content therein. Preferred apparatus is in such a structure that the content therein is transferred forward and particularly preferred one is in such a structure that, when the content is blocked, it is disintegrated as fine as possible so that homogeneous mixing and stirring are possible.

In this step, an apparatus which is a kind of a two-axial paddle type and in which the content can be disintegrated, mixed, stirred and transferred may be used. In the inner part of said apparatus, two rotating axes which rotate and engage each other to inner sides are equipped and, around said rotating axes, paddles are attached and located with a certain interval so that the paddles of the opposite axes bite each other. Function of the paddle is not only to transfer the content forward but also to play a role for disintegrating the solid massceuite, if any, to evaporate the water in the internal part of the block.

In the present invention, it is preferred that the atmosphere in the crystal aging machine is controlled to such an extent of temperature of 70–100° C. and absolute humidity of 50–300 g $H_2O$/kg dry air. For such a purpose, it is necessary that heated and moistened air where temperature and humidity are adjusted as such is introduced into the crystal aging machine so that said machine can keep such an atmosphere. In this step, when crystallization in the massceuite proceeds, water is evaporated to some extent and the moisture content decreases to not more than 3 w/w %. When too quick drying is conducted at the initial stage of crystallization (for example, to an extent of moisture content of 1 w/w % or less), progress of the crystallization becomes significantly slow whereby an object of the present invention cannot be achieved.

In addition, it is preferred that the atmosphere in the inner part of the above crystal aging machine is at a relatively high absolute humidity at high temperature while, at low temperature, it is at a relatively low absolute humidity. When coloring property and crystallizing rate are taken into consideration, it is most preferred that a moistened hot air which is adjusted to the temperature of 85–95° C. and the absolute humidity of 100–200 g $H_2O$/kg dry air is supplied into the inner part of the crystal aging machine. Even when the absolute humidity is made 300 g $H_2O$/kg dry air, aging of the crystals proceeds but their surface seems to be wet partially and the moisture content of the product after completion of the crystal aging is high whereby drying is necessary. With regard to a method of adjusting the heated and moistened air, that which has been commonly used may be adopted and, for example, water in such amount that corresponds to said humidity is sprayed to a heated hot air from a two-fluid nozzle.

Like in the preceding step where the crystallization is promoted by adjusting the crystallizing condition to within a maltitol concentration range of 78–98 w/w %, an object of adjustment of the atmosphere in the inner space of the crystal aging machine is that, during the progress of crystallization in this aging step, anhydrous crystals of maltitol are substantially separated out whereby, in other noncrystalline parts, water content becomes high and solid concentration lowers and, therefore, promotion of aging of the crystals is resulted if the maltitol concentration in the parts other than that where the crystal concentration lowers is maintained within a range of 78–98 w/w %. For increasing the maltitol concentration, further drying and concentration are necessary but, when only dry and hot air is supplied, water is quickly evaporated to result in a syrupy appearance whereupon the crystallization is significantly retarded.

Thus, in the present invention, the atmosphere in the inner part of this crystal aging machine is made in a condition with suitable temperature and humidity by means of the above controlled humid and hot air whereby it is now possible that a drying speed meeting with the progress of crystallization during the crystal aging step is achieved and that anhydrous crystalline maltitol and molasses-containing anhydrous crystalline maltitol powder are obtained within very short time. That is greatly different from the conventional method where crystals are separated out by raising the degree of super-saturation by means of cooling which is a common method for promoting the crystallization of saccharides.

Mixing, stirring and disintegration are essential in this aging step and, if humid and hot air is supplied under the condition of being allowed to stand, the surface becomes to a state of as if being melted and the progress of crystallization is slow whereby long time is needed. Even when the material is transferred using a belt conveyer or the like in an atmosphere of the above-mentioned temperature and humidity, the progress of crystallization is still slow and, accordingly, the necessity of mixing, stirring and disintegration has now been ascertained. If an additional drying step is necessary, hot and dry air is sent into the device used in this aging step to make the moisture content 1 w/w % or less whereby stable anhydrous crystalline maltitol and molasses-containing anhydrous crystalline maltitol are obtained.

EXAMPLES

The present invention will now be more specifically illustrated by way of the following examples although the present invention is not limited thereto.

At first, the experimental examples concerning the decision of the conditions for the steps—heating and concentration, addition and mixing of seed crystals, and aging of crystals—which are the three important steps in the present invention will be mentioned as follows.

From the experiences in the past for the industrial manufacture of anhydrous crystalline maltose, various conditions have chosen with an object of conducting the process within short time on a continuous basis and, taking the conditions, etc. of the machines and apparatuses, a target was set that a step of addition and mixing of the seed crystals, a step of aging the crystals and both steps are to be completed within about 15 minutes, about 30 minutes and at least one hour, respectively. In order to obtain stable anhydrous crystalline maltitol, a target for the step of addition and mixing of the seed crystals was set so as to make the content of crystals after completion of the step not less than 40 w/w % while a target for the step of aging of the crystals was set so as to make the melting point of the product not lower than 120° C. or, preferably, not lower than 130° C.

Experimental Example 1

A seed crystal mixer which will be mentioned in the Examples later was used and 10 w/w % (to the solid in the concentrated solution) of seed crystals were continuously added to and mixed with the concentrated solution whereupon the content of massceuite after the step of addition and mixing of the seed crystals at 110° C. for 15 minutes was measured.

Table 1 shows the result of the massceuite crystal content discharged from the step of addition and mixing of the seed crystals where concentration of maltitol was changed by changing the concentration of the concentrated solution using the samples having varied maltitol purity.

TABLE 1

Relation between Purity/Concentration of Maltitol and Crystal Content of Massceuite after a Step of Addition/Mixing of Seed Crystals

| Maltitol Purity (w/w %) | Concn of Concentrated Solution (w/w %) | Concentration of Maltitol (w/w %) | Crystal Content in the Substance Discharged from a Seed Crystal Addition/Mixing Step (w/w %) |
| --- | --- | --- | --- |
| 94.1 | 80.0 | 75.3 | 30.2 |
| 78.5 | 96.0 | 75.4 | 30.7 |
| 84.0 | 90.1 | 75.7 | 31.5 |
| 80.1 | 95.1 | 76.2 | 31.5 |
| 90.1 | 85.0 | 76.6 | 32.2 |
| 98.5 | 78.1 | 76.9 | 35.0 |
| 78.5 | 98.0 | 76.9 | 36.0 |
| 80.0 | 97.0 | 77.6 | 38.2 |
| 94.1 | 83.0 | 78.1 | 39.5 |
| 98.5 | 80.1 | 78.9 | 41.2 |
| 90.1 | 88.1 | 79.4 | 42.5 |
| 84.0 | 95.0 | 79.8 | 43.2 |
| 84.0 | 97.1 | 81.6 | 43.7 |

TABLE 1-continued

Relation between Purity/Concentration of Maltitol and Crystal Content of Massceuite after a Step of Addition/Mixing of Seed Crystals

| Maltitol Purity (w/w %) | Concn of Concentrated Solution (w/w %) | Concentration of Maltitol (w/w %) | Crystal Content in the Substance Discharged from a Seed Crystal Addition/Mixing Step (w/w %) |
| --- | --- | --- | --- |
| 98.5 | 83.1 | 81.9 | 43.8 |
| 94.1 | 88.0 | 82.8 | 44.2 |
| 90.1 | 93.0 | 83.8 | 45.3 |
| 98.5 | 88.0 | 86.7 | 46.6 |
| 90.1 | 97.1 | 87.5 | 47.8 |
| 94.1 | 93.0 | 87.5 | 48.2 |
| 94.1 | 97.0 | 91.3 | 46.7 |
| 98.5 | 93.0 | 91.6 | 50.5 |
| 98.5 | 97.0 | 95.5 | 45.1 |

It is apparent from the above result that, in the concentrated solution to be supplied in the step of mixing and crystallization of seed crystals, not less than 78 w/w % is necessary as the concentration of maltitol and not less than 80 w/w % is necessary as the purity of maltitol. When such a condition is satisfied, the crystal content in the discharged substance from the seed crystal mixer becomes not less than 40 w/w % and, as a result, the next crystal aging step can be completed within short time whereby an object of the present invention for making the steps short and continuous is possible.

Experimental Example 2

Then, the relation between the atmosphere (temperature and humidity) in the crystal aging machine and the melting point of the aged product in the crystal aging step was investigated.

A maltitol solution having a maltitol purity of 93 w/w % was concentrated to an extent of a maltitol concentration of 87.4 w/w %, supplied to a seed crystal mixer mentioned in the Example at 120° C. and maltitol crystals of 98 w/w % purity as the seed crystals were added thereto in an amount of 10 w/w % to the solid in the concentrated solution and the mixture was mixed by a seed crystal mixer for 15 minutes to give a massceuite containing 48 w/w % of crystals. Another massceuite containing 38 w/w % of crystals was prepared by the same method as well. They were continuously supplied to a crystal aging machine, temperature and humidity of the atmosphere at that time were changed and the melting point of the substance discharged therefrom after aging for 30 minutes was measured. The result is given in Table 2.

TABLE 2

Relation between Atmosphere in Crystal Aging Machine and Melting Point of the Aged Product

| Crystal Content before Aging (w/w %) | Temperature (° C.) | Humidity (g $H_2O$/ kg dry air) | Moisture Content of Aged Product (w/w %) | Melting Point of Aged Product (° C.) |
| --- | --- | --- | --- | --- |
| 48 | 80 | 50 | 1.3 | 124 |
| 48 | 80 | 100 | 1.5 | 125 |
| 48 | 80 | 150 | 1.7 | 122 |
| 48 | 90 | 50 | 1.0 | 119 |

TABLE 2-continued

Relation between Atmosphere in Crystal Aging Machine
and Melting Point of the Aged Product

| Crystal Content before Aging (w/w %) | Temperature (° C.) | Humidity (g H$_2$O/ kg dry air) | Moisture Content of Aged Product (w/w %) | Melting Point of Aged Product (° C.) |
|---|---|---|---|---|
| 48 | 90 | 100 | 1.2 | 130 |
| 48 | 90 | 150 | 1.3 | 137 |
| 48 | 90 | 200 | 1.5 | 134 |
| 48 | 95 | 100 | 0.5 | 119 |
| 48 | 95 | 150 | 0.7 | 125 |
| 48 | 95 | 200 | 1.2 | 133 |
| 48 | 95 | 250 | 1.5 | 135 |
| 48 | 95 | 300 | 1.8 | 131 |
| 48 | 95 | 400 | 2.3 | 119 |
| 48 | 95 | 500 | 3.2 | 118 |
| 38 | 90 | 150 | 0.8 | 113 |
| 38 | 90 | 200 | 1.0 | 114 |
| 38 | 95 | 200 | 0.7 | 113 |
| 38 | 95 | 250 | 1.2 | 110 |

Melting point of the product is one of the indexes for crystallization of anhydrous maltitol and, under the present condition where the maltitol purity was 93 w/w %, the product having a melting point of not lower than 120° C. showed low hygroscopicity and, therefore, "not lower than 120° C." was adopted for the completion of aging of the product as the criteria for passing the test.

It is apparent from the above result that, when the crystal content of massceuite upon supplying to a crystal aging machine is 38 w/w %, a product having a melting point of not lower than 120° C. is not obtained and that, with regard to the absolute humidity of the atmosphere, when that condition is 50–150 g H$_2$O/kg dry air, a product having a melting point of not lower than 120° C. is obtained if the temperature is as relatively low as 80° C. but the higher the humidity, the somewhat lower the melting point. It is also noted that a high-melting point product is obtained at 90° C. if the humidity is 100–200 g H$_2$O/kg dry air and at 95° C. if the humidity is 200–300 g H$_2$O/kg dry air. It is apparent that no desired product is obtained when the humidity is higher or lower than mentioned above. Accordingly, it is clear that the atmosphere in the inner area of the crystal aging machine is to be controlled at 70–100° C. and 50–300 g H$_2$O/kg dry air (absolute humidity) and, within such a range, it is necessary that the lower the temperature, the humidity is to be kept lower and also that the higher the temperature, the humidity is to be kept higher.

Example 1

A starch slurry prepared from corn starch was mixed with a bacterial α-amylase and gelatinized and liquefied by a conventional method and then saccharified by a soybean β-amylase and pullulanase (both manufactured by Nagase Seikagaku), the resulting saccharified solution was concentrated using a vacuum concentrating machine to an extent of 60 w/w % and subjected to a chromatographic separation by Na type cation exchange resin (Japanese Examined Patent Publication Hei-05/2320B), the resulting eluate containing maltose (94.0 w/w % of maltose, 1.7 w/w % of glucose, 2.2 w/w % of maltotriose and 2.1 w/w % of other oligosaccharides; 31 w/w % of solids) was hydrogenated using a Raney nickel catalyst by a conventional method and the resulting maltitol solution mainly comprising maltitol (93.0 w/w % of maltitol, 2.5 w/w % of sorbitol, 2.6 w/w % of maltotriitol and 1.9 w/w % of other sugar alcohols) was treated with a continuous concentrating apparatus of a thin film type as shown in FIG. 1 to give a concentrated solution having a moisture content of 6.4 w/w % where the concentration of maltitol was 87.0 w/w %. Temperature of the concentrated solution and the viscosity at that time were 130° C. and 0.25 Pa.s, respectively. This concentrated solution in a hot state was continuously supplied to a seed crystal mixer and, at the same time, 10 w/w % (to the solid content in the concentrated solution) of anhydrous crystalline maltitol powder (purity: 95 w/w %) as seed crystals were added using a quantitative feeder. This seed crystal mixer was kept at high temperature by heating its jacket using a steam of about 110° C. (142 kPa). Retention time was 15 minutes and moisture content and crystal content in the discharged substance were 6.0 w/w % and 48 w/w %, respectively. Then this discharged substance from the seed crystal mixer was continuously supplied to a crystal aging machine and the atmosphere in the inner part of the crystal aging machine was made in an almost controlled humid and hot condition by supplying a moistened and heated air adjusted at the temperature of 90±2° C. and the humidity of 130 g H$_2$O/kg dry air at a flow rate of 1500 liters per minute at a constant basis to 50 liters of inner space of the crystal aging machine.

The crystal aging machine used is a two-axial paddle type, is capable of mixing, disintegrating and conveying and is equipped with a jacket of 1400 mm length, 250 mm width and 100 liter inner volume. Its inner area is equipped with two rotating axes which rotate in such a manner that they engage each other to the inner side and, around the rotating axes, paddles are located with some intervals so that the paddles of the encountering axes are engaged each other. The function of the paddles is not only that the content therein is moved forward but also that the solidified massceuite, if any, is disintegrated whereby the paddles have a role of evaporating the water in the inner side of the blocks. The number of rotations of the paddle is 30 rpm.

In the inner part of this crystal aging machine kept at the above-mentioned atmosphere condition, the massceuite discharged from the seed crystal mixer was disintegrated as it moved forward while water was appropriately evaporated depending upon crystallizing speed and, after the retention for about 30 minutes, the discharged substance became a crystalline one containing 1.6 w/w % of water. This was ground to give powder which passed a sieve of 10 mesh. Its melting point was as high as 130° C. and the product was very stable powder having little hygroscopicity even when allowed to stand at ambient temperature. All of the above steps after the concentrating step were able to be conducted within as short as about one hour and are convenient for a continuous production.

Example 2

A maltitol solution (containing 92.0 w/w % of maltitol, 2.3 w/w % of sorbitol, 3.3 w/w % of maltotriitol and 2.4 w/w % of other sugar alcohols) obtained by the same method as mentioned in Example 1 was concentrated by a double effect boiler until the solid concentration became 50 w/w %, then supplied to a continuous concentrating apparatus of a thin film type and made into a concentrated solution containing 4.2 w/w % of water and 88.1 w/w % of maltitol. Temperature and viscosity of the concentrated solution at that time were 139° C. and 1.4 Pa.s, respectively. This concentrated solution in a hot state was continuously supplied to a seed crystal mixer and, at the same time, 20 w/w % (to the solid content in the concentrated solution) of molasses-containing anhydrous crystalline maltitol powder (purity: 93 w/w %)

were added as seed crystals whereupon crystallization is conducted with a retention time of 15 minutes to give a product containing 4.0 w/w % and 45.3 w/w % of crystals. This was continuously supplied in a crystal aging step by the same manner as in Example 1 to conduct the aging. The aging condition was that a humid and hot air having a temperature of 90° C. and an absolute humidity of 180 g $H_2O$/kg dry air was supplied by the same flow rate condition as in Example 1. Aging was conducted where the inner area of the crystal aging machine was substantially under said atmospheric condition and the crystalline product obtained by a retention time of 45 minutes contained 0.7 w/w % of water. This was further treated with a grinder to give powder passing through a sieve of 10 mesh. The product was in a powdery state which contained stable crystals having a melting point of 134° C. All steps after the concentrating step were completed within as short as about 75 minutes whereby they can be predominantly applied in continuous production.

Example 3

A maltitol solution (containing 93.2 w/w % of maltitol, 2.2 w/w % of sorbitol, 3.0 w/w % of maltotriitol and 1.6 w/w % of other sugar alcohols; solid content: 30 w/w %) obtained by the same manner as in Example 1 was treated with a continuous concentrating apparatus of a thin film type to give a concentrated solution containing 5.2 w/w % of water and 88.4 w/w % of maltitol. This solution in a hot state was supplied to a seed crystal mixer where the jacket was kept at high temperature by circulating a hot water of 95° C. therein together with continuous addition of 10 w/w % (to the solid content in the concentrated solution) of molasses-containing anhydrous crystalline maltitol powder as seed crystals and, after the retention for about 15 minutes, a massceuite containing 4.9 w/w % of water and 46.5 w/w % of crystals was obtained. This was continuously supplied to a crystal aging machine which was same as that used in Example 1, a humid and hot air controlled at a temperature of 98° C. and an absolute humidity of 250 g $H_2O$/kg dry air was continuously supplied thereto, a crystal aging was conducted in an atmosphere kept at that condition and, after the retention for about 30 minutes, a crystalline product containing 1.8 w/w % of water was obtained. This was treated with a grinder to give a powdery product passing through a sieve of 10 mesh and dried with a hot air drier at 80° C. for 30 minutes to give crystalline powder containing 0.6 w/w % of water. This was a very stable crystalline powder having a melting point of 137° C. All steps after the concentrating step were completed within as short as about 90 minutes whereby they can be predominantly applied in a continuous production.

Comparative Example 1

A comparative experiment was conducted using the apparatus used in Example 1 according to a method mentioned in the Japanese Examined Patent Publication Hei-07/14953B. Thus, the same aqueous solution of maltitol as in Example 1 was used, degree of concentration and temperature of the supplied solution in Example 1 (87.0 w/w % and 130° C.) were changed to 93.8 w/w % and 98° C., respectively, according to the description in the Example of said Japanese patent and, when the temperature of the substance was cooled down to 60° C., about 26 w/w % of seed crystals were added thereto and mixed therewith to give maltitol magma. However, during the process of cooling, viscosity became considerably high and mixing and conveying did not so smoothly take place as those in the examples of the present invention but the product was sent to the crystal aging machine in such a state that the mixing of the seed crystals was still non-homogeneous. Cooling was further conducted in the inner area of the crystal aging machine down to about 40° C. but, as crystals were separated out and temperature was lowered, there was a further increase in the viscosity whereupon mixing, disintegration and transfer did not take place smoothly. Thus, the magma became a block, the transfer did no proceed smoothly, the load of the power for the mechanical stirring became large and, finally, operation of the machine stopped. The content was taken out, spread on a vat made of stainless steel with pulverizing by hand as fine as possible and allowed to stand in a thermostat of 60° C. for about one hour to let it crystallize. Although anhydrous crystals were obtained, the melting point was 118° C. which was not so favorable and, in addition, there is no possibility at all for a continuous operation in an industrial scale. In view of the above, the conclusion is that a method where crystals are separated out by making the solution supersaturated by cooling results in a big load on the machines and apparatuses and that said method is not suitable for conducting it in an expanded scale.

What is claimed is:

1. A continuous manufacturing method for anhydrous crystalline maltitol comprising the following steps:

(i) a heating and concentrating step where an aqueous solution containing maltitol in which maltitol is a main ingredient is continuously heated and concentrated to give a concentrated solution having a high concentration;

(ii) a seed crystal adding and mixing step where the seed crystals are added to and mixed with the above concentrated solution with heating to give a massceuite containing the seed crystals; and (iii) a crystal aging step where the massceuite is subjected to disintegration, mixing, stirring and transfer in an atmosphere in which temperature and moisture are adjusted to proceed the crystallization.

2. A continuous manufacturing method for anhydrous crystalline maltitol according to claim 1 where, in the above heating and concentrating step (i), an aqueous solution in which purity of maltitol is not less than 80 w/w % is made into a concentrated solution containing 78–98 w/w % of maltitol.

3. A continuous manufacturing method for anhydrous crystalline maltitol according to claim 1 where, in the above seed crystal adding and mixing step (ii), the temperature is kept at not lower than 80° C.

4. A continuous manufacturing method for anhydrous crystalline maltitol according to claim 1 where, in the above seed crystal adding and mixing step (ii), the amount of the seed crystals adding to the solid content of the concentrated solution is 5–30 w/w %.

5. A continuous manufacturing method for anhydrous crystalline maltitol according to claim 1 where, upon completion of the above seed crystal adding and mixing step (ii), the content of the crystals in the seed crystal-containing massceuite is not less than 40 w/w %.

6. A continuous manufacturing method for anhydrous crystalline maltitol according to claim 1 where, in the above crystal aging step (iii), the atmosphere is adjusted to a temperature of 70–100° C. and an absolute humidity of 50–300 g $H_2O$/kg dry air.

7. A continuous manufacturing method for anhydrous crystalline maltitol according to claim 6 where the atmo sphere is adjusted to a temperature of 85–95° C. and an absolute humidity of 100–200 g $H_2O$/kg dry air.

8. A continuous manufacturing method for anhydrous crystalline maltitol according to claim 1 where the melting point of the anhydrous crystalline maltitol obtained after completion of the above crystal aging step (iii) is not lower than 120° C.

9. A continuous manufacturing apparatus for anhydrous crystalline maltitol comprising the following means:

(i) a heating and concentrating means where an aqueous solution containing maltitol is continuously heated and concentrated to give a concentrated solution having a high concentration;

(ii) a seed crystal adding and mixing means where the seed crystals are added to and mixed with the concentrated solution by keeping the temperature at not lower than 80° C. to produce a seed crystal-containing massceuite in which the content of the crystals is not less than 40 w/w %; and (iii) a crystal aging means where the massceuite is subjected to disintegration, mixing, stirring and transfer in an atmosphere of temperature of 70–100° C. and absolute humidity of 50–300 g $H_2O$/kg dry air to proceed the crystallization.

* * * * *